United States Patent
Ehrensperger et al.

(12)

(10) Patent No.: US 6,254,065 B1
(45) Date of Patent: Jul. 3, 2001

(54) EVAPORATION DISPENSER HAVING A CONTROL TIMER FOR TIMED RELEASE OF A VOLATILE SUBSTANCE FROM AN EVAPORATION CHAMBER

(75) Inventors: Markus Ehrensperger, Hettlingen; Hans-Jörg Studer, Hittnau, both of (CH)

(73) Assignee: CWS International AG, Baar (CH)

( * ) Notice: Subject to any disclaimer, the term of this patent is extended or adjusted under 35 U.S.C. 154(b) by 0 days.

(21) Appl. No.: 09/481,818

(22) Filed: Jan. 11, 2000

Related U.S. Application Data

(63) Continuation of application No. PCT/CH98/00297, filed on Jul. 7, 1998.

(30) Foreign Application Priority Data

Jul. 11, 1997 (EP) .................................................. 97810462

(51) Int. Cl.[7] ........................................................ B01F 3/04
(52) U.S. Cl. ............................ 261/26; 261/30; 261/104; 261/DIG. 88; 422/124
(58) Field of Search .................................. 261/26, 30, 104, 261/DIG. 17, DIG. 65, DIG. 88; 422/124

(56) References Cited

U.S. PATENT DOCUMENTS

| 4,078,891 | 3/1978 | Madjar ................................. 21/74 R |
| 4,780,253 | 10/1988 | Fukuhara et al. ....................... 261/30 |
| 5,377,363 | * 1/1995 | Shieh ....................................... 4/313 |
| 5,595,324 | * 1/1997 | Brown et al. ............................. 222/1 |
| 5,735,918 | * 4/1998 | Barradas ................................ 55/385.1 |
| 5,894,001 | * 4/1999 | Hitzler et al. ........................... 261/92 |

FOREIGN PATENT DOCUMENTS

| 645148 | 3/1995 | (EP) . |
| 2222775 | 3/1990 | (GB) . |
| 4-165239 | * 6/1992 | (JP) . |
| 5-84285 | * 4/1993 | (JP) ..................................... 422/124 |
| 8000792 | 5/1980 | (WO) . |
| WO90/00231 | * 3/1990 | (WO) .................................. 422/124 |

* cited by examiner

Primary Examiner—David A. Simmons
Assistant Examiner—Robert A. Hopkins
(74) Attorney, Agent, or Firm—Schweitzer Cornman Gross & Bondell LLP

(57) ABSTRACT

An evaporation dispenser for freshening the air in closed spaces such as toilets, washrooms and waiting rooms, telephone booths and lifts. A mounting plate is arranged in a housing and is divided into two chambers by a horizontal separating surface. The lower chamber serves as an evaporation space and holds two bottles of active substance which form a saturated atmosphere in the chamber via evaporating elements. This atmosphere is diffused into the outside air by means of a fan which draws the saturated atmosphere from the evaporation space. Simultaneously, ambient air is drawn into the evaporation space to become saturated. Both the discharge of the saturated atmosphere and the drawing in of ambient air may be performed by a single rotor compressor, the rotor being divided into two sections by a radial divider. The discharge of the saturated atmosphere may be controlled by a microcontroller coupled to sensors which monitor activity in the closed space.

12 Claims, 4 Drawing Sheets

EVAPORATION DISPENSER HAVING A CONTROL TIMER FOR TIMED RELEASE OF A VOLATILE SUBSTANCE FROM AN EVAPORATION CHAMBER

The present application is a continuation of PCT application PCT/CH98/00297 filed Jul. 7, 1998.

The present invention relates to an evaporation dispenser.

BACKGROUND OF THE INVENTION

Deodorizing dispensers (also referred to as air fresheners) can essentially be divided into four categories: those with natural convection of the active substance (air-freshening material); those with mechanically-assisted circulation; those with thermally intensified evaporation of the volatile components of the substance; and room-spray dispensers which spread a fine cloud of droplets by means of a pump operated in bursts (EP-A1-0 127 573 and WO 94/04280).

These latter dispensers intermittently spray an intense cloud of fragrance, but in small rooms. on account of being mounted on or near a door, have the tendency to spray the person entering or leaving the room.

In contrast, another device (WO 80/00792) uses a continuously operated, battery-powered fan which blasts the surface of a liquid active substance and steadily evaporates it. This requires the aerated liquid surface to be at a constant level, which is achieved by means of a liquid supply arranged in the manner of a bird bath, i.e. via a bottle with its mouth immersed in the liquid.

The disadvantage of this device is the constant consumption of active substance, in particular when used in washrooms and/or toilets which are only in intermittent use. In toilets in office buildings, for example. this can also lead to "overperfuming" during the relatively great periods of non-use and, furthermore, requires excessively frequent and uneconomical replacement of the refill bottles containing the active substance. Battery consumption is high; the service intervals needed are therefor very short and may be in the range of a few days.

Hygiene problems also arise; on account of the continuously operating fan, there is a large and continuous supply of germs and the like to the open liquid surface. Viable encrustations in the open containers form.

U.S. Pat. No. 4,078,891 describes an air cleaner connected to a power supply system. The air to be cleaned is drawn in by suction by means of a fan, passes over a filter and is enriched in an inner part of the housing with an active substance and is then discharged. The enrichment occurs over wicks immersed in bottles and/or evaporation tablets on a grid. Underneath the grid is located a relatively large mains operated fan as well as an accompanying electronic controller, which switches the fan sequentially on and off in a predetermined manner.

The disadvantage of this device is the absence of a possibility or requirement-dependent control of function, because the inherently low rate of evaporation allows only short standstill times and therefore makes a mains connection necessary, thus forming a security risk in wet areas such as toilets etc. and calls for special costly installations. Further, outside air streams over the filter through the inner part of the housing and the delivery pipe, even when the fan is switched off, so that the active substance contained therein continuously degrades in an uncontrolled manner.

Therefore, the object of the present invention is to provide a hygienic device which produces an effect precisely adapted to the requirements of the users, which avoids spraying people and, furthermore, is economical to operate and easy to maintain.

In addition, the device should be as versatile as possible and be suitable in particular for toilets, urinals and washrooms. The noise generated by the device should be minimal so that it may also be used in other areas without problem, for example in waiting rooms, lifts, telephone booths, etc.

BRIEF DESCRIPTION OF THE INVENTION

The foregoing and other objects are achieved in the present invention having a volatile active substance for evaporation in a storage container and an evaporating element which allow transfer of the volatile active substance into the atmosphere of a closed evaporation space in the apparatus, the atmosphere reaching saturation. A direct-current motor and compressor withdraws a quantity of the atmosphere saturated with the volatile substance and delivers it into the ambient atmosphere. Saturation of the atmosphere of the closed evaporation space allows the subsequent delivery of the active substance into the ambient atmosphere in an efficient and controlled manner.

The dispenser makes use of the natural, temperature-dependent evaporation capacity of the active substances in the virtually closed evaporation space which is then "ventilated" as required or after use of the environment and its infrastructure (accessible room, toilet, etc.). That is, the atmosphere of the closed evaporation space, saturated with active substance released into the environmental space and is replaced by outside or ambient air which then reaches saturation for a subsequent release.

The time interval between two air changes is defined in accordance with the evaporation rate in the closed evaporation space. In practice, the timing of the emergent air flow can be adjusted according to the average ambient temperature which in turn can be time of year dependent.

The apparatus requires only minimal auxiliary power and ensures almost silent short-time operation.

A suction/delivery fan, which is advantageous from the point of view of energy consumption and effects directional flushing of the evaporation space, has proved successful in use. In addition, the use of two suction and delivery chambers, which are separate from the point of view of flow, can act as labyrinth seals when the rotor is stationary and prevent uncontrolled diffusion of the atmosphere saturated with active substance into the environment.

Two storage bottles provided with suitable evaporating elements permit uninterrupted operation. During the normal service intervals, one bottle allowed to be partially emptied; then a second containing full a supply of active substance is installed. In subsequent intervals the second bottles continues after depletion of the first bottle and a new, full replacement bottle is put in place of the first.

The evaporating elements employed are hygienically satisfactory and can be disposed of without problem while the storage bottles are reusable.

By means of the incorporation of shutters and slides, the admissible or desired emergent volume of evaporated active substance can be adjusted according to the ambient temperature and room size. This results in adjustment of the "background fragrance", which may be produced either through the use of a diffusion port intended for such a purpose or through leakage (lack of tightness) about the rotor of the fan when stationary.

An air inlet may be arranged in the upper portion of the appliance housing. Use of a single rotor fan with a radial partition, which can be manufactured particularly simply and economically, is effective. The fan both evacuates the saturated atmosphere from the evaporation space and drives the new air into the space to be saturated.

The activation of the fan by a sound or motion sensor can results in optimization of duration of operation and running time for the apparatus. By means of a light-sensitive switch, the overall running time of the fan can be further reduced. In addition, the sound sensor (e.g. microphone with quiescent current) and the amplifier connected downstream thereof can be switched off in order to save energy.

Tuning of the sound sensor to the frequencies associated with the environment in which the apparatus is to be used can be particularly advantageous. In toilets and washrooms, the closing of a door and/or the operation of a flush are in particular suitable as detection criteria.

BRIEF DESCRIPTION OF THE DRAWINGS

Preferred but nonetheless illustrative embodiments of the subject of the invention will be described in the following detailed description of the invention, with reference to the annexed drawings, wherein.

DETAILED DESCRIPTION OF THE INVENTION

Figure 1:
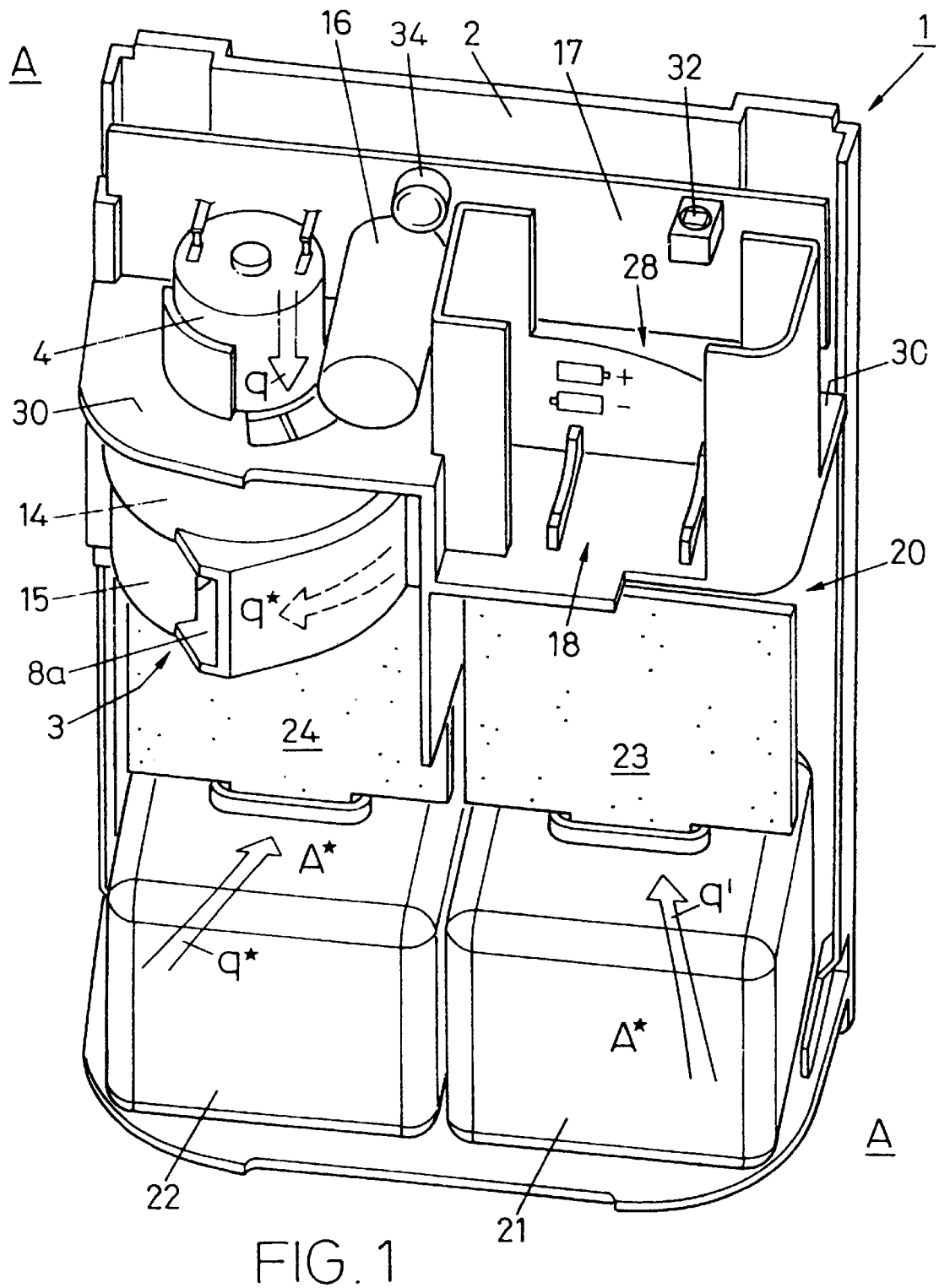
FIG. 1 shows an evaporation dispenser in accordance with the invention with the housing cover removed and with its suction/delivery fan in an oblique view from above.

In FIG. 1, the reference numeral 1 designates an evaporation dispenser, a device for evaporating an active substance as required in accordance with the invention. The dispenser is shown in FIG. 1 with the housing cover removed and is therefore not usable in this form.

The base of the dispenser 1 is formed by a mounting plate 2 which is preferably fixed to a wall. A compressor 3 in the form of a suction/delivery fan with upper and lower chambers is arranged in the top left-hand quadrant. Its drive 4, a miniature direct-current motor, can be seen on top of the compressor 3.

A volume flow q* is indicated in the lower part of the compressor 3 and represents the supply of a saturated atmosphere A* to an exhaust opening 8a from the lower chamber 15 of the compressor 3. The saturated atmosphere A* is developed in the evaporation space 20 by the evaporation of an appropriate commercial active substance therein.

A storage capacitor 16 is arranged next to the drive 4 and, in the variant with a solar module described later, serves as a buffer store for the module. An electronic circuit board 17, carrying inter alia a light-sensitive switch 32, is arranged in the upper part of the mounting plate 2 so as to be parallel thereto. A battery compartment 18 is arranged below the switch 32 and is provided for holding two commercial single cells which, as shown symbolically on the battery compartment rear wall, are connected in series and thus yield 3 V. An air inlet channel 28, which connects the upper chamber of the compressor 3 to the evaporation space 20, is indicated behind the battery compartment 18.

Figure 4:
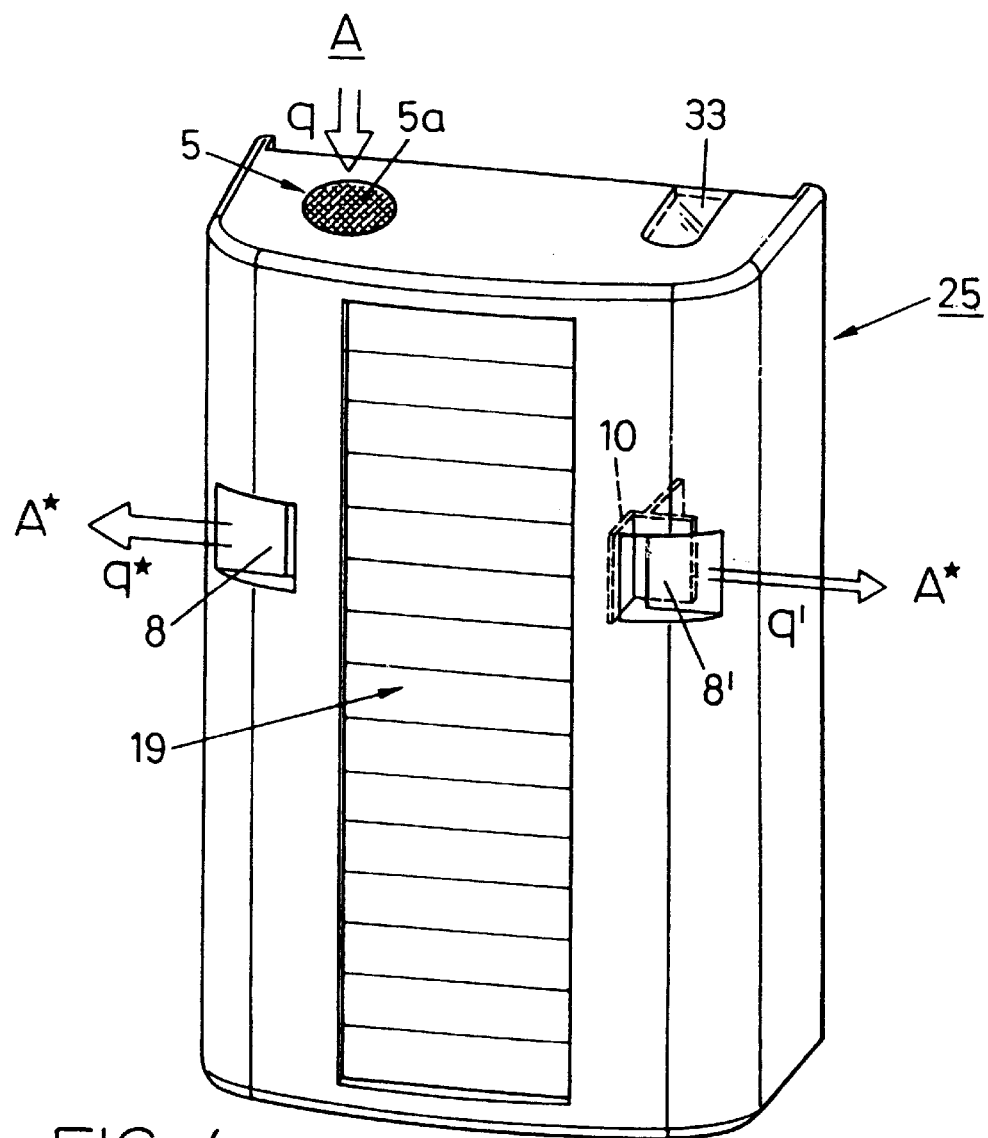
FIG. 4 shows a housing cover of the invention with an air inlet and an exhaust and outlet opening and an incorporated solar module.

With a housing cover 25, cf. FIG. 4, placed onto the mounting plate 2, the evaporation space 20 is formed inside the dispenser 1 and is continuously supplied with the commercial active substance via evaporating elements 23, 24 and storage bottles 21, 22 and consequently develops and contains the aforementioned saturated atmosphere A*.

Figure 2:
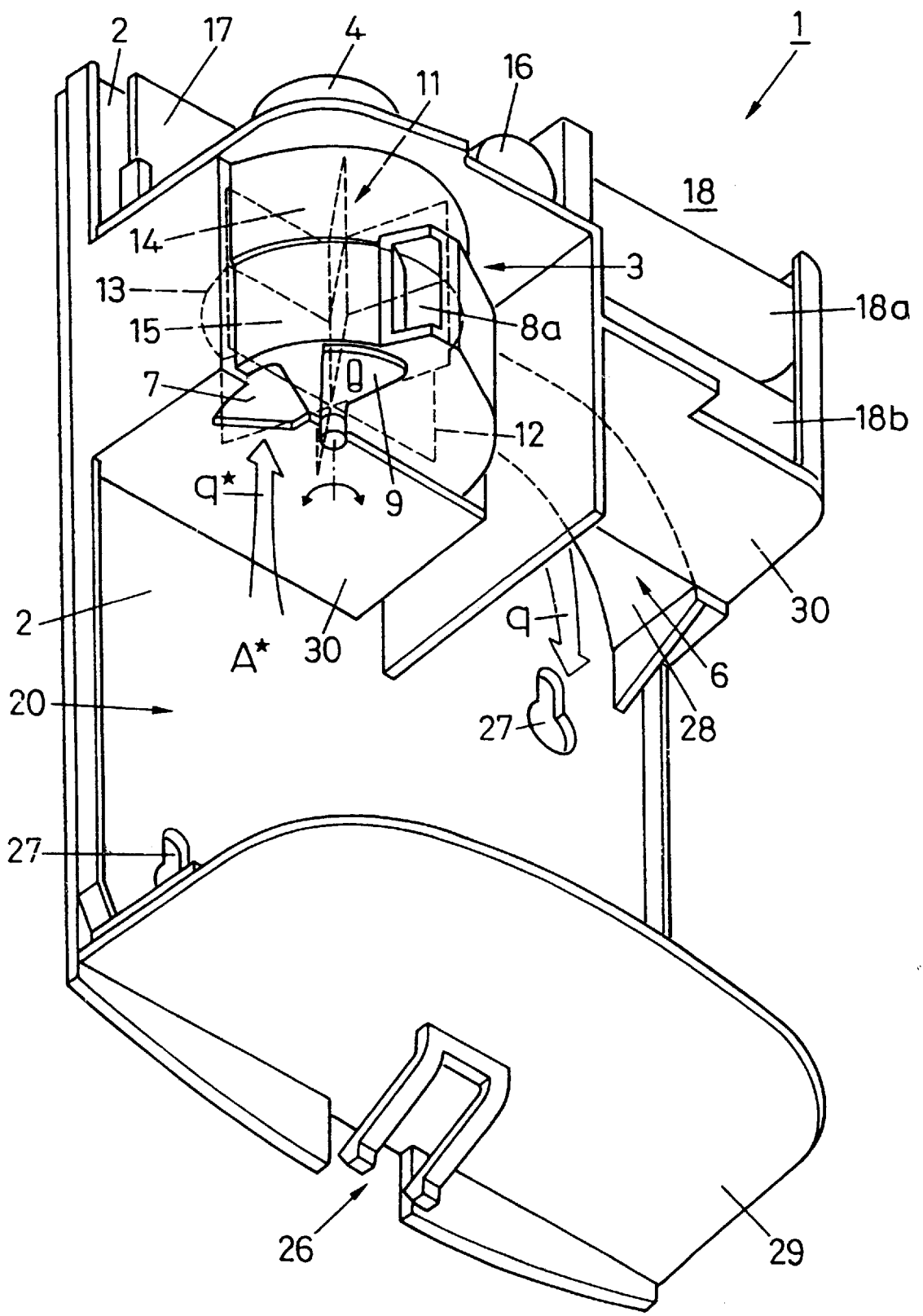
FIG. 2 shows the dispenser according to FIG. 1 with storage bottles removed and with further details in an oblique view from below.

The dispenser 1 is shown with further details in FIG. 2. Here it can be seen how the compressor 3 is constructed and how a single rotor 11 provided therein is arranged with its blades 12 in upper and lower chambers 14 and 15.

The necessary separation between the suction part and the delivery part of the compressor is provided at the rotor 11 by a radial partition 13 which is also indicated. A suction opening 7 for the saturated atmosphere A* is provided below the chamber 15, the suction opening permitting simple adjustment of the output volume flow q* by means of a shutter 9 rotatable on a lever in the direction of the arrow. One of the storage bottles may be located adjacent the suction opening, serving as the primary source for the active substance. In addition, the compressor delivers fresh air to the saturation space 20. The path of the volume flow q with the air supplied to the space 20 by the delivery part can also be seen. The air is drawn in through the delivery part of the compressor 3 through the partly open upper chamber 14 and exhausted into the space 20 the air inlet guide 6 of the inlet channel 28, as indicated by the arrow q. The inlet for this flow into the upper chamber of the compressor can be seen in FIG. 1 below the downward directed flow arrow q by the motor 4.

Two batteries 18a and 18b are also shown. The two slots 27, arranged diagonally to one another and provided for fixing the is dispenser, can also be seen in the mounting plate 2. Below a support 29 carrying the storage bottles 21, 22 is arranged a cover lock 26 which engages in the housing cover 25 when the latter is mounted.

Figure 3:
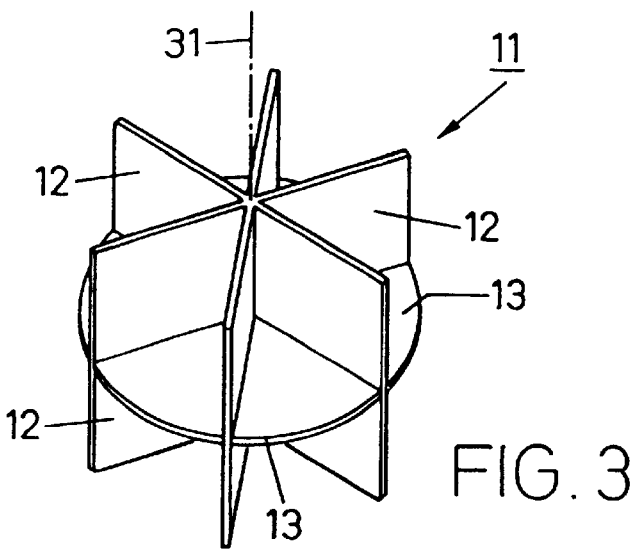
FIG. 3 shows the rotor of the fan in FIGS. 1 and 2.

The rotor 11 is shown in detail in FIG. 3. As may be seen, the radial partition 13. which divides the blades 12 into upper and lower chambers, can also be seen. The rotation axis 31 is merely indicated; it is the motor spindle of the drive 4 which is inserted directly into the rotor 11. The rotor is oriented in the compressor such that the partition maintains a separation between the upper and lower compressor chambers, such that two separate airflow paths through the compressor are maintained. At the same time the saturated atmosphere is exhausted from the space 20 by flow q* a replacement flow q into the space is established.

The housing cover 25 in FIG. 4 belongs to the variant of a dispenser with a solar module 19 formed from a series of individual solar cells as shown. An air inlet 5 with an inlaid filter screen 5a is provided on the left-hand side of the upper end surface of this housing cover 25, and a transparent covering 33. below which the switch 32 in FIG. 1 is arranged, is provided on the right-hand side.

An exhaust opening 8 for the flow q* of the saturated atmosphere A* driven by the delivery part of the compressor, and an outlet opening 8' for a secondary flow q' are provided in the front at the housing cover 25. Behind the slot-type outlet opening 8' is arranged a slide 10 which is used to regulate the volume flow q' to adjust the background fragrance. It is to be appreciated that the background fragrance flow q' is continuous, and results primarily from simple diffusion, rather than the forced air transfer performed by the compressor. The volume flow q of the ambient atmosphere A into the device is also shown.

It can be seen from FIG. 1 in connection with FIG. 4 that the horizontal separating surface 30 divides the dispenser into an upper chamber and a lower chamber serving as the evaporation space 20. The inward air flow q passes through the upper chamber as seen in FIG. 1.

Figure 5:
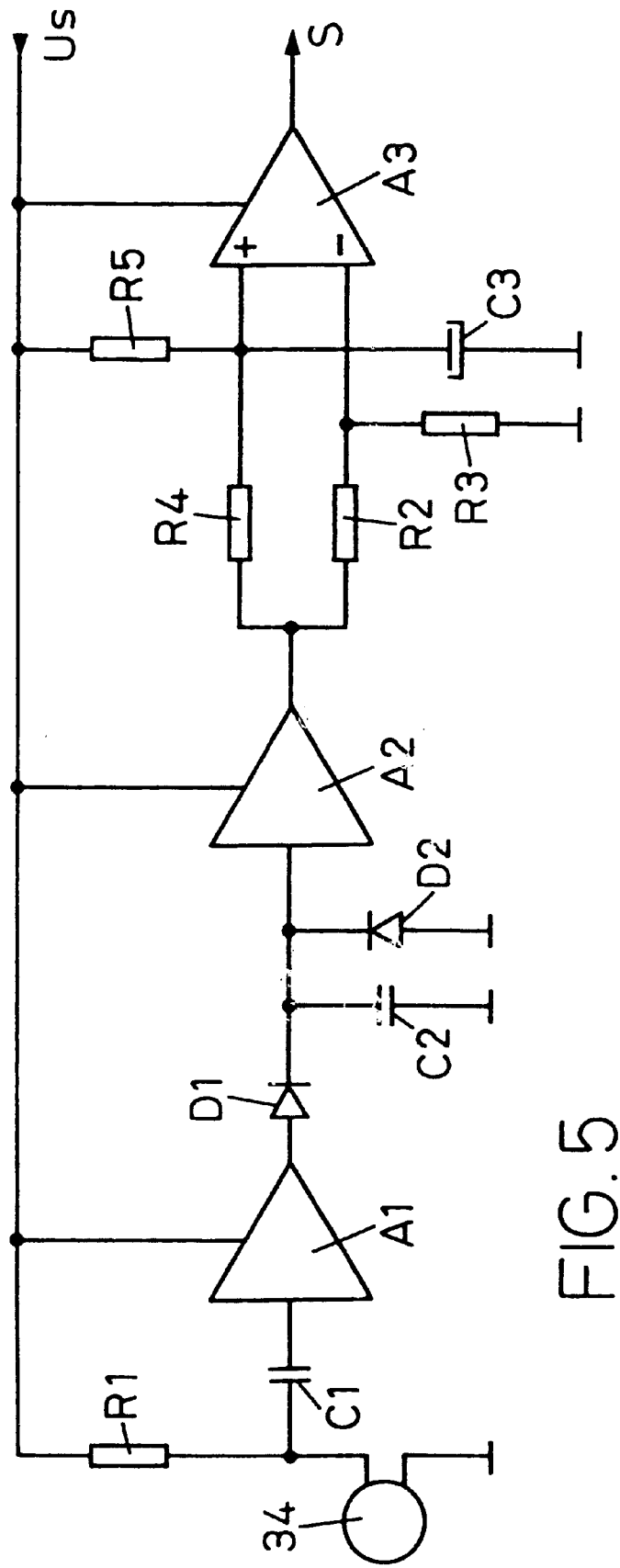
FIG. 5 shows the basic circuit diagram of a microphone and amplifying circuit for detecting use in a room in which the invention is located.

A simplified circuit arrangement is shown in FIG. 5. As shown, a sound sensor 34, such as an electret microphone, detects the need for "fragrancing". The output of the sound sensor 34 is connected via a capacitor C1 to the input of amplifier A1, the output of which leads to the input of a second amplifier A2 via a diode D1 acting as a demodulator. The output of the amplifier A2 leads to a comparator A3, the two inputs of which are connected up via a resistive network R4, R5 for adjusting the minimum response threshold and via a voltage divider R2, R3 which determines the current signal change. The output S of comparator A3 provides a control signal.

The remaining components—resistor R1 and capacitor C3—are arranged in a conventional manner. Resistor R1 determines feedback and thereby the amplifying ratio, which overall may be 1:450. Capacitor C2 and the further diode D2 are components of a filter chain and suppress transient, unwanted signals as known in the art.

The above described circuit of comparator A3 permits the suppression of slowly swelling noise levels and permits only strong acoustic pulses to activate the compressor. The circuit is empirically designed so that the sonic signature of the closing of a door or the operation of a WC flush is evaluated and accepted as a wanted signal and therefore constitutes the message or signal required for activation. A commonly known microcontroller, which generates a signal Us as a control signal for the circuit arrangement according to FIG. 5 in a known manner and which is triggered by the output signal S of the comparator A3, is not shown. When the need for fragrancing is determined, either by the generation of an appropriate output signal S or otherwise, the compressor is activated by the microcontroller for a length of time appropriate to exhaust a quantity of the saturated atmosphere A* from space 20 by the flow q* into the environmental atmosphere. At the same time, the space 20 is refilled by the flow q. The compressor shuts off after the exhaust is completed, and the new atmosphere in the space 20 becomes saturated for the next exhaust cycle.

The above described parts are provided both in the variant with a solar module as well as in a purely battery-powered variant of a dispenser. The variant which is only battery-powered has a housing cover 25 without solar cells and also has no storage capacitor 16. In contrast, the variant with a solar module can do without a light-sensitive switch 32 which can be used in association with a day/night activation control if the day/night circuit is made dependent on the generating power of the solar module 19.

It has been shown that, in practical use, the variant of the dispenser powered purely by batteries can operate without problem for upwards of a year with two single cells, and the variant with a solar module can operate effectively even without batteries.

With a commercial active substance (such as that offered by DRAGOCO, D-37601 Holzminden) and evaporating elements (23, 24) comprising commonly known paper mats and each having a shadow area of 24 $cm^2$, an average running time of the compressor of 3.0 s to 15.0 s at a room temperature of 20° C. has proved satisfactory to provide an exhaust of the saturated atmosphere A*. Depending on the site of use and the time of year, running times of 8.0 s to 20.0 s are appropriate. The time interval between two possible air changes in the evaporation space 20 is set to 4.0 mins. Such an interval is sufficient to obtain adequate saturation in the evaporation space 20 while being able to meet use requirements.

A DIP switch labelled summer and winter and acting directly on the preprogrammed microcontroller can be provided for adjustment of running time.

The above description provided with reference to two practical embodiments can, of course, be expanded and adapted to further embodiment variants. For example, an evaporation dispenser according to the invention can also be arranged on or near a door and be activated by the latter in a simple manner electromechanically or contactlessly by the use of appropriate sensors. In the case of contactless operation of the fan, the direction of closure of a door can also be detected by sensors arranged side by side. Consequently, in the interests of saving active substance, the activation of the fan can be controlled, for example, by closure or opening of the door.

The rotor of the fan can be provided with improved blades with a view to optimizing output; rotor blades which are curved forwards are preferably used. The fan can also be replaced by other suitable compressors, such as diaphragm pumps, piezoelectric conveyors, etc.

The detection of sound sources for activating the fan has proved reliable and sufficiently selective in toilet areas. However, motion detectors of any kind, for example infrared detectors (FIRs), may be appropriate, depending on the site of use and the associated use requirements.

We claim:

1. An evaporation dispenser for releasing at least one deodorizing and/or odor-neutralizing and/or perfuming volatile active substance by evaporating the active substance in a evaporation chamber in the dispenser via at least one evaporating element to form an atmosphere which is enriched with the volatile active substance in the region of the saturation vapor pressure of the substance constituents and releasing at least a portion of the enriched atmosphere in a mechanically accelerated manner into the ambient air during release periods in a range of about 3 to 20 seconds by means of a compressor operated by an autonomously loaded direct current motor, wherein the active substances are contained in at least one storage bottle and the compressor is a suction/pressure fan having a first part for drawing off a quantity of saturated atmosphere from the evaporation chamber and discharging the quantity into the ambient air and a send part for simultaneously supplying a substantially equal quantity of ambient air to the evaporation chamber.

2. An evaporation dispenser according to claim 1, wherein the evaporation chamber has a space for holding two storage bottles with associated evaporating elements, one of the two bottles being placed in a region of a suction opening of the first part of the fan.

3. An evaporation dispenser according to claim 2, wherein an adjustable shutter is mounted upstream of the suction opening.

4. An evaporation dispenser according to claim 1, wherein an air inlet is provided in an upper part of a housing for the dispenser.

5. An evaporation dispenser according to claim 4, further including a further outlet opening in the housing which leads to an evaporation space and has a slide.

6. An evaporation dispenser according to claim 1, wherein the suction/pressure fan has a single rotor provided with a radial partition, dividing the rotor into two separate chambers.

7. An evaporation dispenser according to claim 6, wherein the rotor is driven by the direct-current motor which is powered by an autonomous source and which is switched on via an electronic circuit.

8. An evaporation dispenser according to claim 7, wherein the autonomous source has at least one power source chosen from the group consisting of at least one battery and a solar module.

9. An evaporation dispenser according to claim 7 or 8, further comprising a detector for detecting use of the room coupled to the electronic circuit.

10. An evaporation dispenser according to claim 7 or 8, wherein a light-sensitive switch is provided to deactivate the electronic circuit in the absence of ambient light.

11. An evaporation dispenser according to claim 8, wherein the power source is a solar module for generating electric energy from the light spectrum of artificial light sources and a capacitor associated therewith as a buffer store.

12. An evaporation dispenser according to claim 9, wherein the detector comprises a microphone and a frequency band filter coupled thereto adapted to the characteristic frequencies of requirement-orientated triggering processes and capable of suppressing interference.

* * * * *